United States Patent [19]

Jones

[11] Patent Number: 4,966,976

[45] Date of Patent: Oct. 30, 1990

[54] ISOMERIZATION PROCESS

[75] Inventor: Raymond V. H. Jones, West Lothian, Scotland

[73] Assignee: Imperial Chemical Industries plc, London, England

[21] Appl. No.: 301,020

[22] Filed: Jan. 24, 1989

[30] Foreign Application Priority Data

Jan. 26, 1988 [GB] United Kingdom ............... 8801669

[51] Int. Cl.$^5$ .......................................... C07D 249/08
[52] U.S. Cl. ............................... 548/267.8; 548/268.6
[58] Field of Search ................... 548/262, 267.8, 268.6

[56] References Cited

U.S. PATENT DOCUMENTS 4,639,527  1/1987  Lantzsch et al. ................. 548/262

Primary Examiner—Richard L. Raymond
Assistant Examiner—Patricia L. Morris
Attorney, Agent, or Firm—Cushman, Darby & Cushman

[57] ABSTRACT

Transformation of specified 4H-substituted-1,2,4-triazoles into their 1H-substituted isomers by heating at a temperature of 150° C. to 300° C. in the presence of a base and, essentially, in the absence of a polar aprotic solvent.

8 Claims, No Drawings

ISOMERIZATION PROCESS

This invention relates to an isomerisation process and, more particularly, to a process for transforming a 4H-substituted-1,2,4-triazole into the isomeric 1H-substituted-1,2,4-triazole.

A process for transforming a 4H-beta-hydroxyethyl-1,2,4-triazole derivative into its 1H-isomer is described in EP-A-No. 0143384. The process requires the use of a polar aprotic solvent.

According to the present invention there is provided a process for transforming a 4H-substituted-1,2,4-triazole of the general formula (I):

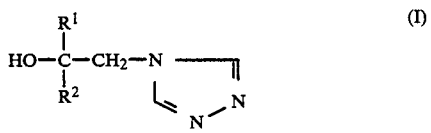

in which $R^1$ is $C_{1-6}$ alkyl, $C_{3-6}$ cycloalkyl, $C_{3-6}$ cycloalkyl($C_{1-4}$)alkyl or optionally substituted phenyl, and $R^2$ is optionally substituted phenyl or benzyl, into the isomeric 1H-substituted-1,2,4-triazole, which comprises heating the triazole of formula (I) at a temperature of from 150° C. to 300° C. in the presence of a base and, essentially, in the absence of a polar aprotic solvent.

Substituents which may be present in phenyl groups or the phenyl moieties of benzyl groups include one or more of halogen (especially chlorine and fluorine), $C_{1-4}$ alkyl, trifluoromethyl, $C_{1-4}$ alkoxy, nitro and phenoxy.

The base is conveniently an alkali metal hydroxide, such as sodium hydroxide or potassium hydroxide, but other bases such as alkaline earth hydroxides and oxides and alkali metal carbonates may be used. Alkali metal alcoholates, tertiary alkylamines and the sodium salt of 1,2,4-triazole may also be used.

The amount of base required should be enough to avoid an unduly slow reaction but there is no upper limit other than what is economical and practicable. The optimum amount can be readily determined by experiment and will depend on the particular base and reaction conditions employed. As an indication, when solid sodium hydroxide is the base, as little as 0.01 mol may be used for each mol of triazole substrate and typically 0.5 to 2 mol up to 25 mol or even 100 mol may be used for each mol of substrate.

The isomerisation is carried out at a temperature of from 155° C. to 300° C., preferably from 155° C. to 220° C. and usually from 160° C. to 190° C. The precise temperature employed will depend inter alia on the nature of the base, whether a diluent is used, the ease of isomerisation and the degree of isomerisation required.

It is necessary only to heat the compound of formula (I) in the presence of a base in the temperature range from 150° C. to 300° C. However, if desired the compound of formula (I) may be suspended or dissolved in a suitable medium such as an organic diluent, provided that the organic diluent is not a polar aprotic solvent as defined in EP-A-No. 0143384, and that it does not react adversely with the triazole derivative under the conditions of the process. The diluent will, therefore, normally be either non-polar or protophilic. Acidic solvents which react with the triazole derivative should be avoided. Suitable diluents include saturated hydrocarbons such as Isopar M (a mixture of $C_{14}$ and $C_{15}$ isoparaffins), polyglycols such as polyethylene glycol (MW 300) and cyclic amines such as 1,2,4-triazole or a salt thereof.

In some cases a diluent may be disadvantageous, for example it may be detrimental to the yield of product obtained, and in a preferred aspect of the invention the process is carried out essentially in the absence of any organic diluent. It may, however, be helpful to have water present, for example 5 to 6 mol per mol of triazole substrate, especially when a solid alkali metal hydroxide base is used. When the sodium salt of 1,2,4-triazole is used as a base and prepared in situ using sodium hydroxide, water will be generated in any case.

The isomerisation may be performed in the presence of the isomeric 1H-substituted-1,2,4-triazole, which generally being more thermodynamically stable than the 4H-substituted-1,2,4-triazole remains unchanged in the reaction mixture. Thus, the process is of especial value in converting the relatively minor proportion, generally around 20% and more usually 15%, or below, of the undesired 4H-substituted-1,2,4-triazole (which is formed during the preparation of a 1H-substituted-1,2,4-triazole by reaction between 1,2,4-triazole or a salt thereof and a compound of formula (II):

in which $R^1$ and $R^2$ have the meanings given before and X is chlorine or bromine or an epoxide derivative of compound (II)) into the desired 1H-substituted-1,2,4-triazole. Moreover, triazolisation of compound (II) or its corresponding epoxide may be performed under the conditions of the present process and reaction continued until sufficient of any unwanted 4H-substituted-1,2,4-triazole has been converted to the 1H isomer.

The process of the invention is of particular interest for compounds of formula (I) in which $R^1$ is n- or t-butyl or phenyl, and $R^2$ is phenyl or benzyl, the phenyl groups and the phenyl moiety of the benzyl group being optionally substituted with fluorine and/or chlorine in the 2- and/or 4-positions of the phenyl ring.

The invention is illustrated, but not limited, by the following Examples in which percentages are by weight.

EXAMPLE 1

Conversion of 1-(2-fluorophenyl)-1-(4-fluorophenyl)-2-(4H-1,2,4-triazol-1-yl)ethanol into 1-(2-fluorophenyl)-1(4-fluorophenyl)-2-(1H-1,2,4-triazol-1-yl) ethanol (a) A dry mixture (3.0 g) of 1-(2-fluorophenyl)-1(4-fluorophenyl)-2-(4H-1,2,4-triazol-1-yl) ethanol (2.89 g) and 1-(2-fluorophenyl)-1(4-fluorophenyl)-2-(1H-1,2,4-triazol-1-yl) ethanol (0.11 g) was placed in a 100 ml round-bottomed flask fitted with a reflux condenser and stirrer. Solid sodium hydroxide (0.46 g) and poly(ethylene glycol) 300 (12.6 g) were added and the mixture heated to 175° C. and maintained at this temperature for two hours.

The product obtained was identified by HPLC analysis as a mixture of 1-(2-fluorophenyl)-1(4-fluorophenyl)-2-(1H-1,2,4-triazol-1-yl) ethanol (0.63 g) and 1-(2-fluorophenyl)-1(4-fluorophenyl)-2-(4H-1,2,4-triazol-1-yl) ethanol (0.05 g); a ratio of 1H-isomer to 4H-isomer of more than 12:1. The yield of the 1H-isomer from starting 4H-isomer was thus 18% (0.63−0.11/2.89×100) and the total yield of 1H- and 4H-isomers was 23% (0.63+0.05/3×100).

(b) The method of Example 1 (a) was repeated except that water (1 g) was present and the reaction temperature was 174° C.

The product obtained was identified by HPLC analysis as a mixture of 1H-isomer (0.69 g) and 4H-isomer (0.11 g); a ratio of more than 6:1. The yield of 1H-isomer from starting 4H-isomer was 20% (0.69−0.11/2.89×100) and the total yield of 1H- and 4H-isomers was 27% (0.69+0.11/3×100).

EXAMPLE 2

Conversion of 1-(2-fluorophenyl)-1(4-fluorophenyl)-2-(4H-1,2,4-triazol-1-yl) ethanol into 1-(2-fluorophenyl)-1(4-fluorophenyl)-2-(1H-1,2,4-triazol-yl) ethanol A dry mixture (2.3 g) of 1-(2-fluorophenyl)-1( 4-fluorophenyl)-2-(4H-1,2,4-triazol-1-yl) ethanol (2.21 g) and 1-(2-fluorophenyl)-1(4-fluorophenyl)-2-(1H-1,2,4-triazol-1-yl) ethanol (0.09 g) was placed in a 100 ml round bottomed flask fitted with a reflux condenser and stirrer. Solid sodium hydroxide (0.6 g), Isopar M (8 g) and water (0.7 g) were added and the mixture heated to 200° C. and maintained at this temperature for 1.5 hours.

The product obtained was identified by HPLC analysis as a mixture of 1-(2-fluorophenyl)-1(4-fluorophenyl)-2 (1H-1,2,4-triazol-1-yl) ethanol (1.41 g) and 1-(2-fluorophenyl)-1-(4-fluorophenyl)-2-(4H-1,2,4-triazol-1-yl) ethanol (0.03 g); a ratio of 1H-isomer to 4H-isomer of 49:1. The yield of 1H-isomer from starting 4H-isomer was thus 60% (1.41−0.09/2.21×100) and the total yield of 1H- and 4-isomers was 63% (1.41+0.03/2.3×100).

1-yl) ethanol (72.9 g), in 12.6% yield, equivalent to a total yield of the isomeric triazoles of 94.9% from epoxide by HPLC determination.

(a) An aliquot of the solution (100 g), containing 1-(2-fluorophenyl)-1-(4-fluorophenyl)-2-(1H-1,2,4-triazol-1-yl) ethanol (27.61 g) and 1-(2-fluorophenyl)-1-(4-fluorophenyl)-2-(4H-1,2,4-triazol-1-yl) ethanol (4.24 g) was distilled under vacuum at 5 mm Hg to a bath temperature of 135° C. to remove dimethylformamide (99% by analysis of analogous material and recovered weight of distillate). Subsequently, under setting for reflux at atmospheric pressure, solid sodium hydroxide (0.3 g) was added to the melt and the bath temperature raised to 190° C., giving an internal temperature of 176° C. The melt was stirred under these conditions for two hours before removing the heating bath and addition of methanol (180 g). The solution was filtered to remove the inorganics and the latter washed twice with further methanol (2×30 g). Analysis of the resulting solution by HPLC was used to determine the levels of the isomeric triazoles. The results are shown in Table I.

(b) A further aliquot (100 g) was treated in the manner of Example 1 (a), but the addition of 0.4 g sodium hydroxide. The results are shown in Table I.

(c) A further aliquot (100 g) was treated in the manner of Example 1 (a), but with the addition of 0.5 g sodium hydroxide. The results are shown in Table I.

(d) A further aliquot (100 g) was treated in the manner of Example 1 (a), but with the addition of 0.8 g sodium hydroxide. The results are shown in Table I.

(e) A further aliquot (100 g) was treated in the manner of Example 1 (a), but with the addition of 1.0 g sodium hydroxide. The results are shown in Table I.

(f) A further aliquot (100 g) was treated in the manner of Example 1 (a), but with the addition of 1.5 g sodium hydroxide. The results are shown in Table I.

TABLE I

| EXAMPLE | BASE (g) | 1H-1,2,4-ISOMER (g) | 4H-1,2,4-ISOMER (g) | TOTAL CONTENT TRIAZOLES (g) | YIELD 1H- + 1,2,4-ISOMER | TOTAL YIELD + TRIAZOLES |
|---|---|---|---|---|---|---|
| * | * | 27.61 | 4.24 | 31.85 | 82.2 | 94.1 |
| 3 (a) | 0.3 | 28.45 | 3.48 | 31.93 | 84.7 | 95.1 |
| 3 (b) | 0.4 | 28.82 | 3.16 | 31.98 | 85.8 | 95.2 |
| 3 (c) | 0.5 | 28.86 | 3.03 | 31.89 | 85.9 | 95.0 |
| 3 (d) | 0.8 | 29.25 | 2.62 | 31.87 | 87.1 | 94.9 |
| 3 (e) | 1.0 | 29.38 | 2.11 | 31.49 | 87.5 | 93.8 |
| 3 (f) | 1.5 | 28.21 | 0.82 | 29.03 | 84.0 | 86.5 |

*Initial aliquot (100 g) of dimethylformamide solution before removal of the solvent.
+Based on starting epoxide.

EXAMPLE 3

Conversion of 1-(2-fluorophenyl)-1-(4-fluorophenyl)-2-(4H-1,2,4-triazol-1-yl) ethanol into 1-(2-fluoro-phenyl)-1-(4-fluorophenyl)-2-(1H-1,2,4-triazol-1-yl) ethanol from a mixture obtained from 1,2-epoxy-1-(2-fluorophenyl)-1-(4-fluorophenyl) ethane and 1,2,4-triazole in dimethyl formamide 1,2-epoxy-1-(2-fluorophenyl)-1-(4-fluorophenyl) ethane (445 g) was reacted with 1,2,4-triazole (159 g) in dimethyl formamide (1043 g) and potassium carbonate (132 g) at 95° C. for 6 hours. The resulting mixture was cooled to 70° C., the inorganic material filtered off and the latter washed with additional dimethyl formamide (180 g). The solution obtained (1718.4 g) contained 1-(2-fluorophenyl)-1-(4-fluoro-phenyl)- 2-(1H-1,2,4-triazol-1-yl) ethanol (474.5 g), in 82.2% yield, and 1-(2-fluorophenyl)-1-(4-fluoro-phenyl)-2-(4H-1,2,4-triazol-

EXAMPLE 4

Conversion of 1-(2-fluorophenyl)-1-(4-fluorophenyl)-2-(4H-1,2,4-triazol-1-yl) ethanol into 1-(2-fluorophenyl)-1-(4-fluorophenyl)-2-(1H-1,2,4-triazol-1-yl) ethanol in a melt containing 1,2,4-triazole To a mixture consisting of 1-(2-fluorophenyl)-1-(4-fluorophenyl)-2-(4H-1,2,4-triazol-1-yl) ethanol (2.13 g) and 1-(2-fluorophenyl)-1-(4-fluorophenyl)-2-(1H-1,2,4-triazol-1-yl) ethanol (0.09 g) was added water (0.7 g), solid sodium hydroxide (6.0 g), and 1,2,4-triazole (6.7 g). This was stirred under reflux at a bath temperature of 200° C., internal temperature of 156° C., for two hours, cooled and then dissolved in methanol (90 g). The resulting solution was filtered and the inorganic cake washed with further methanol (total 50 g). The total solution was analysed by HPLC and found to contain 1-(2-fluorophenyl)-1-(4-fluorophenyl)-2-(1H-

1,2,4-triazol-1-yl) ethanol (0.92 g) and 1-(2-fluorophenyl)-1-(4-fluorophenyl)-1-(4-fluorophenyl)-2-(4H-1,2,4-triazol-1-yl) ethanol (0.11 g), an increase of 0.83 g of 1-(2-fluorophenyl)-1-(4-fluorophenyl)-2-(1H-1,2,4-triazol-1-yl) ethanol, equivalent to a 39% yield based on the initial content of 1-(2-fluorophenyl)-1-(4-fluorophenyl)-2-(4H-1,2,4-triazol-1-yl) ethanol.

EXAMPLE 5

Selective synthesis of 1-(2-fluorophenyl)-1-(4-fluorophenyl)-2-(1H-1,2,4-triazol-1-yl) ethanol from 1,2-epoxy-1-(2-fluorophenyl)-1-(4-fluorophenyl) ethane in a melt containing 1,2,4-triazole 1,2-epoxy-1-(2-fluorophenyl)-1-(4-fluorophenyl) ethane (2.67 g) was stirred with sodium hydroxide (5.60 g) and 1,2,4-triazole (6.90 g) at a bath temperature of 200° C., internal temperature 163°–170° C., for 3 hours. The reaction mass was cooled and methanol (63 g) added to dissolve the melt. The resulting solution was filtered and the inorganic cake washed with further methanol (total 50 g). HPLC analysis of the total solution showed 1-(2-fluorophenyl)-1-(4-fluorophenyl)-2-(1H-1,2,4-triazol-1-yl) ethanol (2.78 g) and 1-(2-fluorophenyl)-1-(4-fluorophenyl)-2-(4H-1,2,4-triazol-1-yl) ethanol (0.04 g), equivalent to a yield of 1-(2-fluorophenyl)-1-(4-fluorophenyl)-2-(1H-1,2,4-triazol-1-yl) ethanol of 80% based on epoxide.

I claim:

1. A process for transforming a 4H-substituted-1,2,4-triazole of the general formula (I):

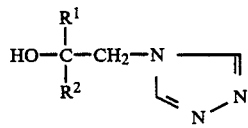
(I)

in which $R^1$ is $C_{1-6}$ alkyl, $C_{3-6}$ cycloalkyl, $C_{3-6}$ cycloalkyl($C_{1-4}$)alkyl, phenyl or substituted phenyl, and $R^2$ is phenyl or substituted phenyl, the phenyl substituents being selected from one or more of halogen, $C_{1-4}$ alkyl, trifluoromethyl, $C_{1-4}$ alkoxy, nitro and phenoxy, into the isometric 1H-substituted-1,2,4-triazole, which comprises heating the triazole of formula (I) at a temperature of from 150° C. to 300° C. in the presence of a base and, essentially, in the absence of a polar, aprotic solvent.

2. A process according to claim 1 which is carried out essentially in the absence of an organic diluent.

3. A process according to claim 1 in which the base is an alkali metal hydroxide.

4. A process according to claim 3 in which the base is sodium hydroxide.

5. A process according to claim 1 in which water is present.

6. A process according to claim 1 in which there is present initially with the 4H-substituted-1,2,4-triazole an amount of the corresponding 1H-isomer.

7. A process according to claim 6 in which the 4H-isomer forms 20% or less of the total amount of 4H- and 1H-isomer initially present.

8. A process according to claim 1 in which the 4H-substituted-1,2,4-triazole has the formula:

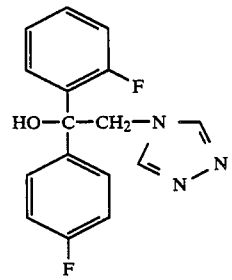

* * * * *